United States Patent [19]

Kouno et al.

[11] Patent Number: 5,284,560
[45] Date of Patent: Feb. 8, 1994

[54] ACID DYE STAINING METHOD

[75] Inventors: Naoyuki Kouno; Jun Suzuoki, both of Amagasaki, Japan

[73] Assignee: Wako Pure Chemical Industries, Ltd., Osaka, Japan

[21] Appl. No.: 902,626

[22] Filed: Jun. 23, 1992

[30] Foreign Application Priority Data

Jun. 24, 1991 [JP] Japan .................. 3-178788

[51] Int. Cl.$^5$ .............. G01N 27/26; G01N 27/447; G01N 33; G01N 48; G01N 21/75
[52] U.S. Cl. .................. 204/182.8; 204/180.1; 204/299.00 R; 8/506; 436/86; 436/166
[58] Field of Search ............. 204/182.8, 180.1, 299 R; 8/506; 436/86, 87, 88, 164, 166, 169

[56] References Cited

U.S. PATENT DOCUMENTS

| | | | |
|---|---|---|---|
| 4,023,933 | 5/1977 | Bradford et al. | 436/87 |
| 4,405,720 | 9/1983 | Merril | 436/86 |
| 5,064,768 | 11/1991 | Ebata et al. | 436/86 X |

FOREIGN PATENT DOCUMENTS

| | | | |
|---|---|---|---|
| 56-069556 | 6/1981 | Japan . | |
| 56-103366 | 7/1981 | Japan | 436/86 |

OTHER PUBLICATIONS

Analytical Biochemistry 152, pp. 308–313, 1986.
Analytical Biochemistry 20, pp. 150–154, 1967.
Anthony T. Andrews "Electrophoresis: Theory, Techniques, and Biochemical and Clinical Applications" 2nd ed. 91986) p. 28.

*Primary Examiner*—John Niebling
*Assistant Examiner*—John S. Starsiak, Jr.
*Attorney, Agent, or Firm*—Armstrong, Westerman, Hattori, McLeland & Naughton

[57] ABSTRACT

An acid dye staining method for electrophoretically separated fractions on a supporting matrix characterized by fixing the supporting matrix after electrophoresis with an aqueous solution containing a lower alcohol and an organic acid, followed by staining with an acid dye solution mixed with at least one specified acid, can reduce a time required for staining remarkably and improve the sensitivity greatly.

9 Claims, No Drawings

ACID DYE STAINING METHOD

BACKGROUND OF THE INVENTION

This invention relates to a modified acid dye staining method used for detection of fractions of proteins, etc. separated by electrophoresis, and a reagent solution used therefor.

Fractions of proteins, etc. separated by electrophoresis are usually colorless, and hence their staining with dyes, etc. is always conducted for detection an identification.

For example, amido black 10B (C.I. No. 20470), Coomassie brilliant blue R-250 (C.I. No. 42660) and Acid Violet 17 (C.I. No. 42650) are widely used as acid dyes for staining in dark blue, light blue and light purple, respectively. However, in staining with these acid dyes, the dyes intrude into and settle in a get itself though not bound thereto through stationary bounds such as chemical bonds, so that a colored background appears. Therefore, destaining of the background is indispensable. The destaining is conducted usually by immersion with shaking in a methanol-water mixed solution containing acetic acid or trichloroacetic acid. Although depending on the kinds of the dye used and the gel and other conditions of the staining, the time required for the destaining is at least 4 hours. For making the destaining perfect, the time is usually longer, namely, 6 to 7 hours. The time required for the staining is 2 to 4 hours in practice though a little shorter in some modified methods. Therefore, the total time required exceeds a working day.

On the other hand, Analytical Biochemistry 20, 150 (1967) describes a modified method in which staining is carried out by placing trichloroacetic acid together with Coomassie brilliant blue R-250 immediately before use. Analytical Biochemistry 152, 308 (1986) describes a modified method in which staining is carried out by adding picric acid to the above dye. In the former method, the staining can be carried out in 1 hour, but a destaining procedure is indispensable and the sensitivity is low. In the latter method, the staining can be carried out in 30 minutes, but this method has a serious defect in that destaining of the background requires twice as much time as that usually required, owing to hindrance by the yellow color of picric acid. This method involves a problem of the danger of handling picric acid at a starting material for a reagent solution.

Thus, staining with the acid dyes requires a troublesome procedure and a long time, but it is undeniable that the staining is now the most reliable, useful and frequently used method for detection and identification of fractions separated by electrophoresis.

SUMMARY OF THE INVENTION

An object of this invention is to provide a method which can omit the above-mentioned troublesome operations in the useful acid dye staining method for electrophoretically separated fractions on a supporting matrix, reduce the time required for treatment in this method, and further improve performance characteristics of this method heretofore attained. Another object of this invention is to provide a reagent solution used in the method provided.

This invention provides an acid dye staining method for electrophoretically separated fractions on a supporting matrix which comprises fixing the supporting matrix after electrophoresis with an aqueous solution containing a lower alcohol having 1 to 4 carbon atoms and an organic acid; and then staining the supporting matrix with an acid dye solution containing one or more acids selected from the group consisting of dicarboxylic acids, amino acids, hydroxy acids, sulfonic acids and kojic acid.

This invention also provides a reagent solution for acid dye staining after electrophoresis which comprises an acid dye solution and one or more acids selected from the group consisting of dicarboxylic acids, amino acids, hydroxy acids, sulfonic acid and kojic acid.

This invention further provides a kit for acid dye staining after electrophoresis comprising (a) as a reagent solution for fixation an aqueous solution containing a lower alcohol having 1 to 4 carbon atoms and an organic acid, and (b) the above-mentioned reagent solution for staining.

DESCRIPTION OF PREFERRED EMBODIMENTS

The present inventors earnestly investigated in order to achieve the above objects, and consequently found that staining with an acid dye solution containing one or more specified organic acids makes it possible to suppress staining of a supporting matrix itself sufficiently and make unnecessary or limit extremely a procedure of destaining the background. Furthermore, the present inventors found that the reduction of the time required for staining and the enhancement of the sensitivity can be achieved by subjecting a supporting matrix after electrophoresis to fixation with an aqueous solution containing a lower alcohol having 1 to 4 carbon atoms and an organic acid, before the above specified staining procedure, whereby this invention has been accomplished.

As the supporting matrix for electrophoresis to which the method of this invention is applied, there are usually used those composed of a material having a network structure. There can be exemplified those composed of macromolecular substances such as polyacrylamide gels, agarose gels, agar gels, cellulose acetate strips, etc.

The lower alcohol having 1 to 4 carbon atoms used for the fixation according to this invention includes methanol, ethanol, propanol, isopropanol, isobutanol, etc. The organic acid used for the fixation includes monocarboxylic acids such as formic acid, acetic acid, propionic acid, etc., and all of various organic acids usable in the undermentioned staining treatment according to this invention.

Although the concentrations of the lower alcohol and the organic acid in the reagent solution for the fixation are not critical, the concentration of the lower alcohol is usually about 5 to about 70 v/v %., preferably about 15 to about 60 v/v %, and the concentration of the organic acid is usually about 5 to about 30 w/v %, preferably about 10 to about 20 w/v %.

The fixing procedure as pretreatment can be carried out merely by immersing the supporting matrix after electrophoresis in an aqueous solution containing the lower alcohol and the organic acid (hereinafter abbreviated as "the fixing reagent solution") with shaking for a predetermined time. Although the volume of the fixing reagent solution is usually 5 times or more as large as that of the supporting matrix, it is usually preferably about 10 times as large as the volume of the supporting matrix because use of too large a volume of the fixing reagent solution means a waste of the reagent. Although it is usually sufficient that the fixation is carried out once, it is preferable to carry out the fixation once more by replacing the solution by a fresh one. Although the time of the fixation is not critical, it is usually sufficient that the fixation is carried out twice for about 10 minutes each time.

As the acid dye used for the staining in this invention, there can be exemplified all of acid dyes usually used in the art, for example, Coomassie brilliant blue R-250 (C.I. No. 42660), Coomassie brilliant blue G-250 (C.I. No. 42655), Acid Violet 17 (C.I. No. 42650), amido black 10B (C.I. No. 20470), Nigrosine (C.I. No. 50420), Ponceau 3R (C.I. No. 16155), etc. Of these dyes, Coomassie brilliant blue R-250 and Acid Violet 17 are particularly preferable. Although the concentration of the acid dye is not critical, it is usually about 0.01 to about 1.5 w/v %, preferably about 0.05 to about 1.0 w/v %.

The structural formulas for the above-named acid dyes are as follows:

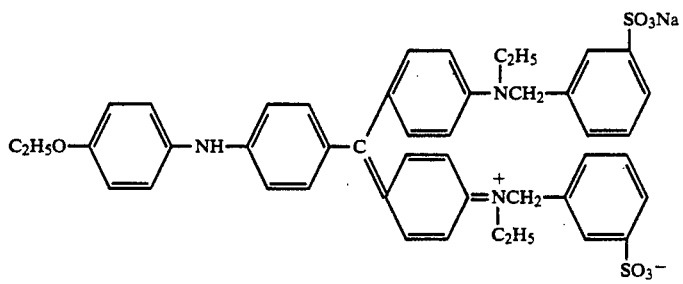
Coomassie Brilliant Blue R-250

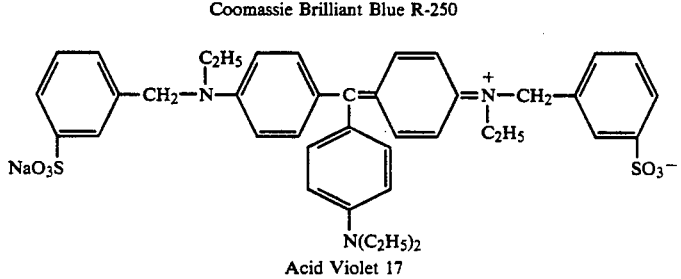
Acid Violet 17

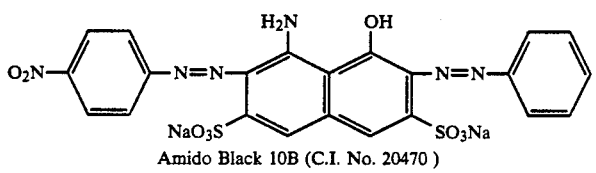
Amido Black 10B (C.I. No. 20470)

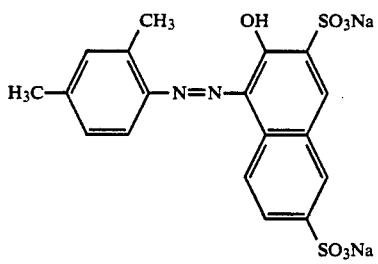
Ponceau 3R

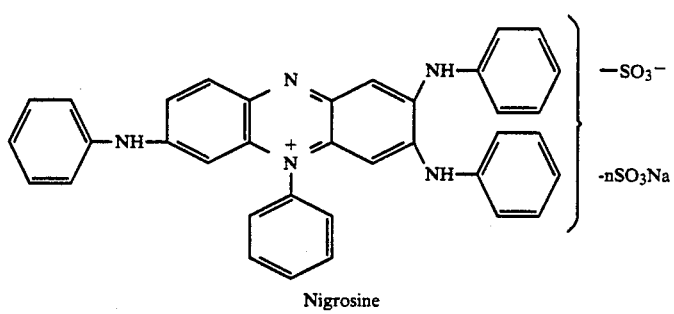
Nigrosine

The staining method of this invention is characterized by using an acid dye solution containing one or more specified organic acids in addition to an organic acid (e.g. acetic acid, etc.) optionally used for dissolving the dye.

The concentration of the organic acid for dissolving the dye changes depending on the kind of organic acids used and is usually 1 to 30 v/v % or more. For example, in the case of acetic acid, the concentration is preferably about 3 to 20 v/v %, more preferably about 5 to 10 v/v %.

As the specified organic acid contained in the acid dye solution in this invention, the following can be exemplified: aliphatic or aromatic dicarboxylic acids such as succinic acid, oxalic acid, adipic acid, glutaric acid, malonic acid, pimelic acid, suberic acid, azelaic acid, sebacic acid, fumaric acid, maleic acid, itaconic acid, phthalic acid, etc.; amino acids such as aspartic acid, glutamic acid, glycine, alanine, etc.; aliphatic or aromatic hydroxy acids such as lactic acid, tartaric acid, citric acid, mandelic acid, malic acid, tartronic acid, glyceric acid, α-oxybutyric acid, glycolic acid, β-hydroxybenzoic acid, gallic acid, protocatechuic acid, orsellinic acid, salicylic acid, etc.; aliphatic or aromatic sulfonic acids such as sulfoacetic acid, methanesulfonic acid, β-toluenesulfonic acid, benzenesulfonic acid, sulfosalicylic acid, etc.; and kojic acid which is a special organic acid. These specified organic acids can be used singly or as a mixture thereof.

Although the content of the specified organic acid in the acid dye solution is not critical, it is usually about 0.1 to about 5 w/v %, preferably 0.3 to 3 w/v %. The reagent solution for staining of this invention is used usually in a volume of 2 to 10 times, preferably 3 to 8 times, more preferably 3 to 5 times, as large as the volume of the supporting matrix.

The staining method of this invention comprises subjecting a supporting matrix supporting substances (e.g. proteins, polyepitides, etc.) to be detected thereon and having been subjected to electrophoresis, to the above-mentioned fixing procedure according to this invention, and then to staining treatment with the present invention's reagent solution for staining comprising the aforesaid acid dye, an organic acid (e.g. acetic acid, etc.) optionally used for dissolving the dye, and the aforesaid specified organic acid. As the time required for said staining treatment, about 30 minutes is usually sufficient.

Thus, when there are used the acid dye staining method of this invention and the reagent solution for acid dye staining of this invention (or the present invention's kit using said reagent solution which comprises the reagent solution for fixation and the reagent solution for staining), destaining which has been considered indispensable and requires a long time, usually becomes unnecessary. In this case, when destaining of the background is desired for some reason, for example, intentional or accidental staining for a long period of time, it can be conducted using a conventional reagent solution for destaining (an aqueous solution or a methanol-water mixed solution, which contains acetic acid or trichloroacetic acid), and a destaining treatment for about 10 minutes is sufficient unlike in conventional methods.

This invention is explained below with reference to Examples and Comparative Examples, which are not by way of limitation but by way of illustration.

EXAMPLE 1

An aqueous solution (a solution in deionized water; hereinafter the same applied) containing 45 v/v % of methanol and 10 w/w % of acetic acid was prepared as a reagent solution for fixation. A reagent solution for staining was obtained by adding Coomassie brilliant blue R-250 to a 10 w/v % acetic acid aqueous solution to adjust the concentration of the dye to 0.2 w/v %, and mixing the solution thus prepared with a 2 w/v % oxalic acid aqueous solution in a volume ratio of 1:1.5. Separately, a 10 w/v % acetic acid aqueous solution was used as a conventional reagent solution for destaining.

As a sample, a polyacrylamide gel having bovine serum protein electrophoresed thereon was immersed with shaking in the reagent solution for fixation (in a volume of 10 times the volume of the gel) twice for 10 minutes each time. Next, the gel was immersed with shaking in the reagent solution for staining (in a volume of 4 times the volume of the gel) for 30 minutes and then in the reagent solution for destaining for 10 minutes. The total time required for the above procedure was 60 minutes. The stain image obtained was excellent. The highest sensitivity of the part could easily be attained. The sensitivity was such that when the total amount of proteins was 0.075 μg, clear bands appeared.

In the present example, a sufficiently detectable and identifiable, clear stain image could be obtained even when the last procedure, i.e., the destaining procedure was omitted.

EXAMPLE 2

An aqueous solution containing 60 v/v % of ethanol and 20 w/v % of tartaric acid was prepared at a reagent solution for fixation. A reagent solution for staining was obtained by adding Coomassie brilliant blue R-250 to a 10 w/v % acetic acid aqueous solution to adjust the concentration of the dye to 0.05 w/v %, and mixing the solution thus prepared with a 3 w/v % tartaric acid aqueous solution in a volume ratio of 1:1.2. Separately, as in Example 1, a 10 w/v % acetic acid aqueous solution was used as a reagent solution for destaining.

Using the above reagent solution for fixation reagent solution for staining and reagent solution for destaining, a commercially available molecular weight marker comprising phospholylase B, bovine serum albumin, ovalumin, carbonic anhydrase, soybean trypin inhibitor, and lysozyme was treated in the same manner as in Example 1 to obtain the same results as in Example 1.

EXAMPLE 3

An aqueous solution containing 15 v/v % of isopropanol and 15 w/v % of citric acid was prepared as a reagent solution for fixation. A reagent solution for staining was obtained by adding Coomassie brilliant blue R-250 to a 10 w/v % acetic acid aqueous solution to adjust the concentration of the dye to 1.0 w/v %, and mixing the solution thus prepared with a 0.5 w/v % kojic acid aqueous solution in a volume ratio of 1:2.5. Separately, as in Example 1, a 10 w/v % acetic acid aqueous solution was used as a reagent solution for destaining.

Using the above reagent solution for fixation, reagent solution for staining and reagent solution for destaining, rabbit IgG F(ab')$_2$ was treated in the same manner as in Example 1 to obtain the same results as in Example 1.

EXAMPLE 4

An agarose gel having bovine serum protein electrophoresed thereon was treated as a sample in the same manner as in Example 1, except that exactly the same reagent solutions as in Example 2 were used except for using glycine in place of tartaric acid in the reagent solution for staining used in Example 2. Consequently, the same results as in Example 1 were obtained.

EXAMPLE 5

An agar gel having bovine serum protein electrophoresed thereon was treated as a sample in the same manner as in Example 1 by using exactly the same reagent solutions as in Example 1 except for using salicylic acid in place of oxalic acid in the reagent solution for staining. Consequently, the same results as in Example 1 were obtained.

EXAMPLE 6

An agar gel having bovine serum protein electrophoresed thereon was treated as a sample in the same manner as in Example 1 by using exactly the same reagent solutions as in Example 1 except for using sulfoacetic acid in place of oxalic acid and using Acid violet 17 in place of Coomassie brilliant blue R-250 in the reagent solution for staining. Consequently, the same results as in Example 1 were obtained.

EXAMPLE 7

The process of Example 1 was repeated except for using citric acid in place of oxalic acid in the reagent solution for staining. Consequently, the same results as in Example 1 were obtained.

COMPARATIVE EXAMPLE 1

Convention Method 1

As a reagent solution for staining, a solution was prepared by adding amido black 10B to a 7 w/v % acetic acid aqueous solution to adjust the concentration of the dye to 1 wt %. An aqueous solution containing 50 v/v % of methanol and 10 w/v % of acetic acid was used as a reagent solution for destaining.

A polyacrylamide gel having bovine serum protein electrophoresed thereon was immersed as a sample with shaking in the aforesaid reagent solution for staining for 15 minutes. In the gel thus stained, the whole gel including the background has been stained, so that detection and identification of objective fractions was utterly impossible unless the background was destained. The destaining could be substantially achieved b immersing the stained gel with shaking in the aforesaid reagent solution for destaining for 4 hours. A satisfactory stain image could be obtained, but the sensitivity was such that when the total amount of proteins was 0.75 $\mu$g, clear bands appeared.

COMPARATIVE EXAMPLE 2

Conventional Method 2

As a reagent solution for staining, a solution was prepared by adding Coomassie brilliant blue R-250 to an aqueous solution containing 10 w/v % of acetic acid and 45 v/v % of ethanol, to adjust the concentration of the dye to 0.25 w/v %. An aqueous solution containing 10 w/v % of acetic acid and 45 v/v % of ethanol was used as a reagent solution for destaining.

A polyacrylamide gel having bovine serum protein electrophoresed thereon was immersed as a sample with shaking in the aforesaid reagent solution for staining for 15 minutes. In the gel stained, the whole gel including the background had been stained, so that detection and identification of objective fractions was utterly impossible unless the background was destained. The destaining could be substantially achieved by immersing the stained gel with shaking in the aforesaid reagent solution for destaining for 4 hours. Consequently, the same results as in Example 1 were obtained.

COMPARATIVE EXAMPLE 3

An aqueous solution containing 10 w/v % of acetic acid and 45 v/v % of methanol was prepared as a reagent solution for fixation. As a reagent solution for staining, a solution was prepared by adding Coomassie brilliant blue R-250 to a 10 w/v % acetic acid aqueous solution to adjust the concentration of the dye to 0.1 w/v %. An aqueous solution containing 10 w/v % of acetic acid and 45 v/v % of ethanol was used as a reagent solution for destaining.

A polyacrylamide gel having bovine serum protein electrophoresed thereon was immersed as a sample with shaking in the aforesaid reagent solution for fixation twice for 10 minutes each time. Then, the gel was immersed with shaking in the reagent solution for staining for 30 minutes. In the gel stained, detection and identification of objective fractions was utterly impossible unless the background was destained. The destaining could be substantially achieved by immersing the stained gel with shaking in the aforesaid reagent solution for detecting for 4 hours. Consequently, the same results as in Example 1 were obtained.

COMPARATIVE EXAMPLE 4

A reagent solution for staining was obtained by adding Coomassie brilliant blue R-250 to a 10 w/v % acetic acid aqueous solution to adjust the concentration of the dye to 0.2 w/v %, and mixing the solution thus prepared with a 2 w/v % oxalic acid aqueous solution in a volume ratio of 1:1.5. Separately, a 10 w/v % acetic acid aqueous solution was used as a conventional reagent solution for destaining.

A polyacrylamide gel having bovine serum protein electrophoresed thereon was immersed as a sample with shaking in the aforesaid reagent solution for staining for 30 minutes, and then in the reagent solution for destaining for 10 minutes. A satisfactory stain image could be obtained, but the sensitivity was such that when the total amount of proteins was 7.5 $\mu$g, clear bands appeared.

COMPARATIVE EXAMPLE 5

The following experiment was carried out according to the method described in Analytical Biochemistry 20, 150 (1967), to obtain the results described below.

A 12.5 w/v % trichloroacetic acid aqueous solution was used as a reagent solution for fixation. A reagent solution for staining was prepared by diluting a 1 w/v % Coomassie brilliant blue R-250 aqueous solution in 20 times with a 12.5 w/v trichloroacetic acid aqueous solution. A 12.5 w/v % trichloroacetic acid aqueous solution was used as a reagent solution for destaining.

An agarose gel having bovine serum protein electrophoresed thereon was immersed as a sample with shaking in the aforesaid reagent solution for fixation for 30 minutes and then in the reagent solution for staining for 30 minutes. In the gel thus obtained, the whole gel including the background had been stained, so that detection and identification of objective fractions wa almost impossible unless the background was destained. The destaining could be substantially achieved by immersing the stained gel with shaking in the aforesaid reagent solution for destaining for 1 hour. A satisfactory stain image could be obtained, but the sensitivity was such that when the total amount of proteins was 0.75 μg, clear bands appeared.

The results of Examples 1 to 7 and Comparative Examples 1 to 5 are shown in Table 1.

TABLE 1

| Example No. | Staining | | Destaining | |
| --- | --- | --- | --- | --- |
| | Staining[1] time (min) | Detecting[2] sensitivity | Destaining time (min) | Detecting sensitivity |
| Example 1 | 50 | ++++ | 10 | ++++ |
| Example 2 | " | " | " | " |
| Example 3 | " | " | " | " |
| Example 4 | " | " | " | " |
| Example 5 | " | " | " | " |
| Example 6 | " | " | " | " |
| Example 7 | " | " | " | " |
| Comparative Example 1 | 15 | — | 240 | +++ |
| Comparative Example 2 | 15 | — | 240 | ++++ |
| Comparative Example 3 | 50 | — | 240 | ++++ |
| Comparative Example 4 | 30 | ++ | 10 | ++ |
| Comparative Example 5 | 60 | + | 60 | +++ |

Note)
[1] Time is a total of a fixing time and a staining time.
[2] Detecting sensitivity:
++++: Clear bands appeared at the total protein amount of 0.075 μg.
+++: Clear bands appeared at the total protein amount of 0.75 μg.
++: Clear band appeared at the total protein amount of 7.5 μg.
+: No clear band appeared at the total protein amount of 7.5 μg.
—: No clear band appeared.

As explained above, by carrying out fixation with an aqueous solution containing a lower alcohol having 1 to 4 carbon atoms and an organic acid before acid dye staining, and then conducting the acid dye staining in the presence of one or more acids selected from the group consisting of dicarboxylic acids, amino acids, hydroxy acids, sulfonic acids and kojic acid, the time required for the staining is greatly reduced, staining of the background is suppressed to such an extent that subsequent destaining is made substantially unnecessary, and the sensitivity is markedly enhanced. This result is quite beyond expectation, as compared with the following result obtained for the method decreased in the reference [Analytical Biochemistry 20, 150 (1967)] which uses Coomassie brilliant blue R-250 in combination with trichloroacetic acid: although staining of the background is suppressed to a certain extent, staining of fractions is also suppressed, so that a new problem of low sensitivity is caused.

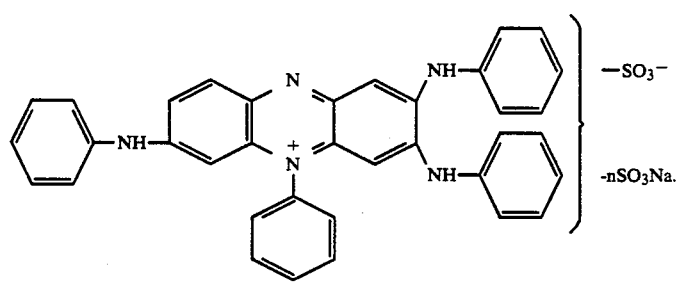

What is claimed is:

1. An acid dye staining method for electrophoretically separated fractions on a supporting matrix which comprises fixing the supporting matrix after electrophoresis with an aqueous solution containing a lower alcohol having 1 to 4 carbon atoms and an organic acid, and staining the supporting matrix with an acid dye solution containing at least one acid selected from the group consisting of dicarboxylic acids, amino acids, hydroxy acids, sulfonic acids and kojic acid.

2. The method according to claim 1, wherein the supporting matrix is a polyacrylamide gel.

3. The method according to claim 1, wherein the supporting matrix is an aqueous gel or an agar gel.

4. The method according to claim 1, wherein the specified acid is at least one member selected from the group consisting of oxalic acid, tartaric acid, citric acid, kojic acid, glycine, salicylic acid and sulfoacetic acid.

5. The method according to claim 1, wherein the acid dye is of the formula.

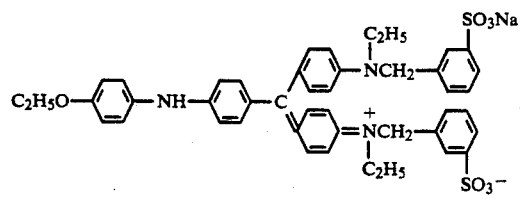

6. The method according to claim 1, wherein the acid dye is of the formula.

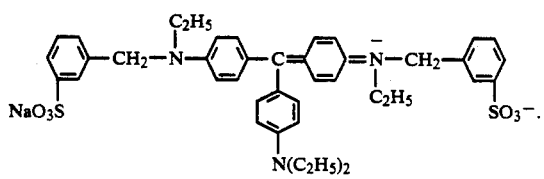

7. The method according to claim 1, wherein the acid dye is of the formula.

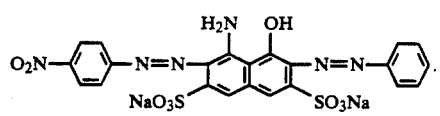

8. The method according to claim 1, wherein the acid dye is of the formula.

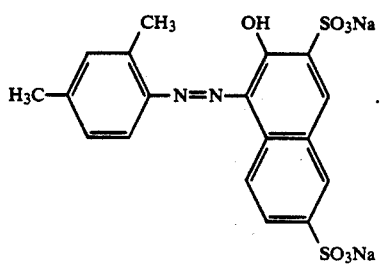

9. The method according to claim 1, wherein the acid dye is of the formula.